(12) United States Patent
Shusterman (10) Patent No.: US 8,706,464 B2
(45) Date of Patent: Apr. 22, 2014

(54) HEALTH DATA DYNAMICS, ITS SOURCES AND LINKAGE WITH GENETIC/MOLECULAR TESTS

(76) Inventor: Vladimir Shusterman, Pittsburgh, PA (US)

( * ) Notice: Subject to any disclaimer, the term of this patent is extended or adjusted under 35 U.S.C. 154(b) by 191 days.

(21) Appl. No.: 13/017,043

(22) Filed: Jan. 30, 2011

(65) Prior Publication Data

US 2011/0190598 A1 Aug. 4, 2011

Related U.S. Application Data

(60) Provisional application No. 61/300,004, filed on Jan. 31, 2010.

(51) Int. Cl.
*G06G 7/58* (2006.01)
*G01N 33/48* (2006.01)
*G06F 17/50* (2006.01)

(52) U.S. Cl.
USPC .................................. 703/11; 702/19; 703/13

(58) Field of Classification Search
None
See application file for complete search history.

(56) References Cited

U.S. PATENT DOCUMENTS

| | | | |
|---|---|---|---|
| 4,475,554 A | 10/1984 | Hyndman | |
| 4,807,638 A | 2/1989 | Sramek | |
| 4,869,262 A | 9/1989 | Orr | |
| 5,709,212 A | 1/1998 | Sugo et al. | |
| 6,413,223 B1 | 7/2002 | Yang | |
| 7,179,228 B2 | 2/2007 | Banet | |
| 2008/0221419 A1 | 9/2008 | Furman | |

FOREIGN PATENT DOCUMENTS

| | | |
|---|---|---|
| EP | 0443267 A1 | 8/1991 |
| EP | 1150604 B1 | 8/2007 |

*Primary Examiner* — Eric S Dejong (57) ABSTRACT

Method and system for the analysis and source localization of the dynamical patterns in medical and health data, and linking such dynamical patterns with the individual's genetic and/or molecular data. The invention makes use of optimally positioned sensors (sensor arrays) providing input data for signal processing, time-series analysis, pattern recognition and mathematical modeling to facilitate dynamical tracking of systemic arterial pressure without a pressure cuff, local vascular activity, electrocardiographic (ECG), respiratory, physical, muscular, gastrointestinal and neural activity, temperature and other physiological/health data. The invention also facilitates separation of local signals (such as local aneurisms or local vascular activity) from non-local, central or systemic patterns (e.g. systemic blood pressure). In addition, the invention improves identification of dynamical patterns associated with a specific genotype/disorder for screening, personalized risk assessment, diagnosis and treatment control. The system can be implemented in a specialized processor, such as an ambulatory blood pressure monitor, Electrocardiograph, Holter monitor located outside subject's body or implanted inside the body, mobile/cell phone or Smart Phone/Personal Digital Assistant, computer or computer network (the Internet), including wireless or mobile network. The system can be also linked to the electronic health/medical records and other databases.

19 Claims, 3 Drawing Sheets

RMSSD = the square root of the mean of the differences in successive RR-intervals; Filtering cutoffs = the thresholds for including RR-intervals. P values are for the comparisons between the two cutoffs (Wilcoxon test). N = number of patients. SE = standard error.

HEALTH DATA DYNAMICS, ITS SOURCES AND LINKAGE WITH GENETIC/MOLECULAR TESTS

CROSS REFERENCE TO RELATED APPLICATION

This application claims the benefit of U.S. Provisional Application Ser. No. 61/300,004, filed on Jan. 31, 2010, the disclosure of which is fully incorporated by reference herein.

FIELD OF THE INVENTION

This invention relates to the field of medical information management, diagnosis, and decision support and, more specifically, to a method and system for the analysis and source localization of the dynamical patterns in medical and health data (in the electrocardiographic (ECG), respiratory, physical-activity, muscular-activity, gastrointestinal-activity, neural-activity, temperature and other physiological/health data), and linking such dynamical patterns with the knowledge of individual's genetic and/or molecular data using adaptations of signal processing, time-series analysis or pattern recognition methods and systems. The invention also relates to the field of differential diagnosis between local dynamical patterns associated with a specific anatomical structure or organ located near a measurement sensor(s) versus non-local or systemic dynamical patterns generated by physiological processes (sources) located further away from the measuring sensor(s), such as systemic arterial pressure, cardiac output, autonomic nervous system activity, hormonal influences or circadian rhythmicity.

BACKGROUND OF THE INVENTION

In 2008, Roytvarf and Shusterman (IEEE Trans Biomed Eng. 2008; 55 (2):407-18) reported on the development and validation of a mathematical model for dynamical tracking of cardiovascular homeostasis (including systemic blood pressure, cardiac output and systemic peripheral resistance). In that 2008 report, Roytvarf and Shusterman have also disclosed a system for measuring arterial pressure waveforms and pulse-transit time (i.e. the time required for arterial-pressure wave to travel between any two points of the arterial system), to provide input data for the mathematical model. That system used the (photo-) plethysmographic sensor on one of the fingers to measure the pressure waveforms and the ECG sensors to determine the time of occurrence of the R-wave (as a surrogate for the start time of the arterial pressure wave). The same study also demonstrated substantial variability in peripheral vascular activity (measured on one of the fingers), which complicated dynamical tracking of systemic arterial pressure patterns.

Similar disorders might have different dynamical patterns of health data, clinical manifestations and prognoses in patients with different genetic variants. For instance, cardiac arrhythmias and sudden death in Long QT type 1 are usually associated with intense physical activity (swimming) or emotions, whereas in Long QT type 3 and Brugada syndrome, arrhythmias and sudden death usually occur during sleep or at rest. The traditional electrocardiographic (ECG) analysis has identified typical ECG changes associated with these disorders; for example, a long QT-interval on the ECG is a hallmark of the Long QT syndrome. However, the characteristic dynamical patterns and their relationships to the genetic variants, mutations and genetic polymorphisms, gene and protein expression levels are largely unknown. The predictive value of such dynamical patterns associated with different genetic sub-types currently is also unknown.

SUMMARY OF THE INVENTION

Dynamical Tracking of Arterial Pressure, Cardiac Output, Vascular Activity, and Differential Diagnosis of Arterial/Aortic Aneurisms This invention provides methods and system for dynamical tracking of systemic arterial pressure, cardiac output, vascular activity and other patterns of cardiovascular activity, its homeostasis and regulation. In addition, it facilitates analysis of the physiological origins of such patterns, which may originate from systemic sources (e.g. systemic arterial pressure) or local anatomical structures (e.g. local vascular activity near the measurement sensor).

This invention further extends the methods and system disclosed in the 2008-study by Roytvarf and Shusterman described above (IEEE Trans Biomed Eng. 2008; 55(2):407-18) to improve the accuracy of arterial pressure monitoring by eliminating confounding effects of peripheral vascular activity. These confounding effects are eliminated by measuring the arterial pressure-waves in the central arteries with a relatively low contribution of vascular activity. The measurement sensors are placed near central blood vessels (e.g. abdominal aorta, carotid arteries, kidney arteries, femoral arteries or hepatic portal vein). This approach facilitates differentiation of local (e.g., peripheral vascular) versus central (systemic) dynamical patterns, including the patterns of systemic blood pressure, cardiac output, vascular and autonomic nervous system activities, and hormonal influences, as described above.

Localization and Separation of Sources of Dynamical Patterns in Health Data

The method and system of this invention facilitate discrimination of local dynamical patterns of a particular internal organ or anatomical structure from non-local dynamical patterns "transmitted" or "irradiated" to that organ from distant anatomical structures, organs or systemic sources.

For example, separating the dynamical patterns of systemic arterial pressure from local vascular activity near the measurement sensor and local changes in the vascular wall that could be related to atherosclerosis, fibrosis, or an aneurism is technically difficult. Another example is the dynamics of heart rate determined by: i) local cardiac properties and structures and, in particular, the properties of its sinus node (for example, the sick sinus syndrome is manifested by the heart rate irregularities), and ii) external influences of the central nervous system, autonomic nervous system (sympathetic and parasympathetic/vagal effects on the sinus node) and neurohormonal effects. Because the resulting patterns of heart rate dynamics represent a combination of such local and non-local effects, separating the sources of those diverse effects is technically difficult.

This invention provides a method that allows the separation of such local from non-local dynamical patterns. Specifically, the present invention facilitates: i) identification of characteristic features of local and non-local (external, central) dynamical patterns of health data, ii) adjustments of the model parameters, filtering cutoff values, diagnostic thresholds or coefficients of a mathematical transform, such as Fourier transform or principal component analysis or parameters/variables in a mathematical function to achieve either: a) an optimal separation between local and non-local dynamical patterns/effects or b) detection and dynamical tracking of a specific pattern concealed within a multi-component group of effects. Once those optimal functions/models/parameters are identified, they can be used for personalized tracking of each dynamical pattern associated with a specific physiological source (either local or non-local) concealed within a complex, multi-component dynamics of a biological system, such as the cardiovascular circulation. Example 1 below shows how to separate specific types of heart-rhythm irregularities associated with a local (cardiac) sinus node dysfunction in patients with Brugada syndrome. Specifically, the method presented in Example 1 makes use of the idea that centrally mediated dynamical patterns of heart rhythm (associated with changes in the autonomic nervous system activity, circadian rhythmicity or hormonal effects) are usually "smooth" and gradual, without extreme jumps or irregularities. This assumption is supported by a wealth of evidence from experimental, clinical and theoretical studies that examined heart rate variability patterns in various settings and identified specific frequency ranges associated with sympathetic and parasympathetic (vagal) effects. In particular, sympathetic effects are slower (<0.15 Hz), whereas vagal effects are faster (0.15-0.4 Hz). In contrast, pronounced irregularities and sudden "jumps" in the beat-to-beat series of cardiac cycles or RR-intervals, whose frequency is >0.4 Hz or undetermined (highly-irregular pattern) and which are not associated with any environmental, physiological, biochemical or psychological changes, are usually a sign of a local dysfunction in the cardiac sinus node, such as the sick sinus syndrome. Thus, the method described in Example 1 detects and quantifies such pronounced irregularities of beat-to-beat series of cardiac cycles, which represent different genetic variants of sinus node dysfunction, by using multiple filtering cutoffs.

Other potential applications include separation of:
  obstructive (local) from central sleep apnea and corresponding (local versus central) sleep disordered breathing;
  physiological responses to physical activity, daily activities, psychological or mental stress, which could be due to central/autonomic nervous system effects or local (cardiac) physiological processes;
  dynamical patterns of sleep and sleep disorders that can be associated with central/autonomic nervous system effects or sleep disordered breathing (the latter can be also associated with local, obstructive sleep apnea or central apnea);
  QT-interval adaptation to changes in heart rate, physical activity, mental stress or circadian (24-hour) cycling, which can be related to local (cardiac effects) and non-local (neurohormonal effects);
  local/non-local/central origins of dynamic physiological instabilities, including dynamic instabilities in the cardiac function (such as T-wave alternans, instabilities of the STT-segment on the ECG and other electrophysiological instabilities of the heart), central (brain) or peripheral nervous system (including autonomic ganglia), instabilities of vascular tone and blood pressure;
  local/non-local/central circadian effects that may include central/autonomic/neurohormonal effects or local cellular circadian "clock" genes/proteins.

Dynamical Pattern Recognition Linked to Genetic Data (DPRL-Gene)

This invention also provides a method and system, herein referred to as the Dynamic Pattern Recognition Linked to Genetic Data (DPRL-Gene) that can be used for at least one of information management, decision support and diagnosis. This method and system identifies or extracts typical (characteristic) features of dynamical patterns of an individual's health data and associates these typical features of dynamical patterns with an individual's genetic variants, genetic polymorphisms, mutations, genomic, proteoimic and metabolomic data, using an adaptation of signal-processing, pattern-recognition and time-series-analysis methods described below. Examples of an individual's health data include an electrocardiogram (ECG), respiratory activity, neural activity, physical activity, temperature, blood pressure, vascular activity, baroreflex, vagus-nerve response or activity, sympathetic nerve response or activity, other autonomic nervous system reflexes, responses or activity, gastrointestinal activity, muscular tone, as well as combinations of various data types.

DPRL-Gene links the dynamical patterns of health data to the specific genetic variants and/or molecular data by adapting the parameters/ranges of the signal-processing (pattern-recognition, time-series-analysis) techniques to the characteristics of those dynamic data patterns associated with specific genetic variant(s), as illustrated in Examples shown below. The examples of dynamical patterns (time series) include: 1) individual waveforms, for example, the ECG waveforms, and/or 2) derived parameters/indices, including the electrocardiographic P-wave amplitude/duration, PQ-intervals, QRS-intervals, T-wave amplitudes, T-wave alternans, QT-intervals, and other parameters derived from the dynamic data representing vascular tone, blood pressure, central neural activity, peripheral neural activity, autonomic nervous system activity, muscular activity, skin resistance or impedance, thoracic impedance, temperature, gastrointestinal activity, respiration or sleep disordered breathing, physical activity, and sleep patterns.

DPRL-Gene can be implemented using hardware or software, or a combination of hardware and software tools; it can be also distributed along a network, which can be a router-based or mobile (including a cell phone, smart phone, personal digital assistant (PDA) or a specialized mobile computing/communication device). It may also include the Internet, local computer network (such as intranet), Wi-Fi, Bluetooth or other communication protocols for data transmission and communication.

The method and system can be used as:
  Hospital or medical center information management;
  Information management for ambulatory patients;
  Information management for community health program;
  Information management for corporate health program;
  Self-awareness and health advice system;
  Information management for patients with implantable devices;
  Medical decision support system for medical professionals implemented on a personal computer, a cell phone, a smart phone, or a personal digital assistant (PDA);
  Information management or decision support system that includes personalized analysis of serial data and medical knowledge contained in medical literature and on the Internet;
  Personalized advice system implemented on a personal computer, a cell phone, a smart phone, or a personal digital assistant (PDA);
  First-aid health-data analyzer for emergency units, paramedics, and medical personnel;
  Health data analyzer for a routine medical examination;
  A personal one-time or serial data analyzer with storage of individual historic data, adaptive adjustment of individual thresholds and assessment of changes in individual heath pattern;
  A one-time or serial health-data analyzer for a group of people, a family or a patient group, with storage of individual historic data for each person, adjustment of individual thresholds and assessment of changes in individual health patterns;

Event-monitoring device including patient-detected events;

Bedside monitoring;

Bedside or ambulatory monitoring providing intelligent alarms to medical professionals when appropriate;

At least one of arrhythmia, stress-test, ischemia, ST-segment, and T-wave alternans monitoring;

Pacemaker and other implantable device checking, bi-directional or uni-directional communication, programming, and control;

Evaluation of the treatment efficacy, side effects and progression of the disease.

Linking the Sources of Dynamical Patterns of Health Data to Genetic/Molecular Data Another application of this invention is to identify the links between the sources of dynamical patterns of health data (described above) and genetic/molecular variants.

In particular, a dynamical pattern originating from a specific source can be statistically associated (correlated) with a particular genetic variant. Then, the signal-processing/filtering cutoffs/model parameter/mathematical functions can be adjusted to separate/detect such genetic variants and associated dynamic health-data patterns. Example 1 illustrates how local dynamic patterns of the sinus node dysfunction in the heart can be linked to specific genetic variants of Brugada syndrome.

Another potential application of this invention is linking of non-local (autonomic nervous system or hormonal) patterns of cardiac rhythm dynamics to a specific genetic variant. Additional potential applications are: i) linking a local dynamic pattern of vascular dynamics to a specific genetic variant, ii) linking a non-local dynamic instability of blood pressure/vascular tone regulation to a specific genetic variant, iii) linking a local dynamic pattern/instability of cardiac (atrial or ventricular) repolarization, including T-wave alternans, non-alternating forms of STT-segment instabilities (oscillating at other frequencies), changes/instabilities in QT-intervals, T-wave patterns/morphology, ST-segment, QRS-complex, and P-wave on the electrocardiogram to a specific genetic variant, iv) linking/separating the genetic variants associated with obstructive (local) sleep apnea and non-local (central) sleep apnea, sleep disordered breathing and other sleep patterns, v) separating and linking the genetic variants associated with local (cardiac, vascular) vs. non-local (autonomic nervous system, hormonal, blood pressure) dynamical patterns/effects associated with physical activity, sleep, psychological stress, mental stress, and daily activities.

This invention also provides methods and system for determining/associating the probability of having a particular genetic variant in the presence or absence of a certain dynamical pattern. Such a probability can be determined by using Bayesian probability, in which the probability of having a particular genetic variant G given a certain dynamical pattern X (P(G|X) is proportional to the product of the conditional probability of observing the dynamical pattern X in the presence of the particular genetic variant G (P(X|G)) multiplied by the prior probability of observing the genetic variant G (P(G)) and divided by the marginal probability of observing the dynamical pattern X (P(X)):

$$P(G|X) = \frac{P(X|G) \cdot P(G)}{P(X)} \quad (1)$$

which can be also expressed as:

$$P(G|X) = \frac{P(G \cap X)}{P(X)} \quad (2)$$

For a composite dynamical pattern, a probability can be estimated using a hidden Markov model as described in the Shusterman's patent application Ser. No. 12/885,520; the disclosure contained in that application is, by reference, incorporated herein in its entirety.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

One embodiment of this invention uses the following sequence of steps for tracking arterial pressure dynamics: i) a model of systemic arterial pressure regulation is constructed as described by Roytvarf A. and Shusterman V. in "A large-scale, energetic model of cardiovascular homeostasis predicts dynamics of arterial pressure in humans," published in IEEE Trans Biomed Eng. 2008; 55(2):407-18; ii) parameters, thresholds and filtering cutoff values are adjusted to achieve the best (optimal) discrimination between an individual's systemic (central) dynamical patterns of arterial pressure and cardiac output versus the patterns of peripheral vascular activity, as described in Examples 1 and 2 below and by the signal-processing, pattern-recognition, statistical, mathematical modeling and time-series analysis methods described in the U.S. Pat. Nos. 6,389,308; 6,925,324, and 7,343,197 to Shusterman; and iii) the model is used for either tracking of such systemic/central dynamical patterns of arterial pressure and cardiac output or subtracting those systemic, non-local patterns to expose the residual local activity (in the vicinity of measurement points).

This invention extends the 2008-study by Roytvarf and Shusterman by determining an optimal location for a sensor that registers the pressure wave. The sensors can be adapted from at least one accelerometer, microphone, micro-electro-mechanical (MEMS) sensor, plethysmographic, photoplethysmographic, acoustic, ultrasound, infrared, magnetic, electromagnetic, pulse oximetry sensor, registering at least one mechanical movement, acceleration, acoustic signals or changes in the light intensity and other electromechanical, electromagnetic and electrochemical sensors, registering mechanical movements, acceleration, acoustic signals or changes in the light intensity, changes in electromagnetic, electromechanical or electrochemical field or activity. In particular, the sensor that registers the pressure wave can be placed on the torso instead of (or in combination with) a sensor placed more peripherally (extremities, fingers, etc). Because vascular activity is predominantly present in the peripheral vessels, placing the sensor for measuring the pressure pulse wave on the torso eliminates the vascular-activity confounder and simplifies the detection, separation and tracking of non-local (systemic) patterns of blood pressure dynamics, which are primarily associated with changes in the cardiac output, heart rate and systemic vascular activity. In addition, placing the sensor in the vicinity of central blood vessels also facilitates the detection of changes in those blood vessels. For example, placing the sensor in the vicinity of abdominal aorta will facilitate detection of an aneurism or atherosclerotic impairment in the abdominal aorta. Similarly, placing the sensor for tracking pressure wave in the vicinity of the portal vessels will improve the detection and tracking of the portal pressure changes and an early detection of the dynamic patterns associated with portal hypertension, cirrhosis or other liver disorders. Similarly, placing the sensor for tracking pressure wave in the vicinity of pulmonary vessels (large pulmonary arteries/veins) will improve the tracking of pressure changes in the pulmonary-artery/venous system. For example, the sensor can be placed over the right lung (to provide some distance from the heart).

Figure 3:
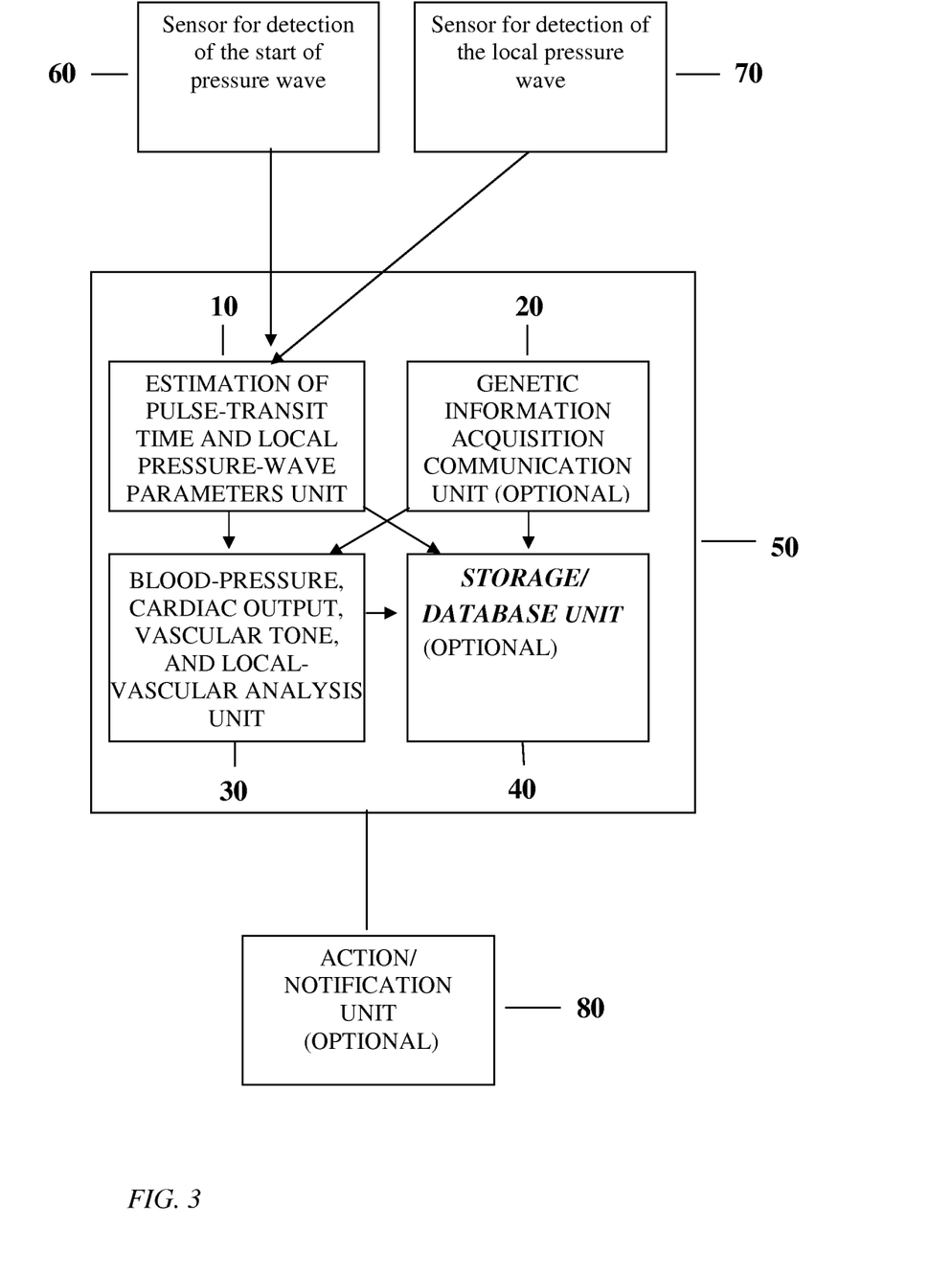
FIG. 3 is a block diagram of another important embodiment of the method and system of this invention for tracking the dynamic patterns of at least one of: systemic blood pressure, cardiac output, peripheral resistance/vascular compliance, pulmonary-artery pressure, portal-system pressure, pulmonary edema, and aneurisms of aorta.

To achieve an optimal detection of the pulse-pressure signal, the sensor for registering the pressure wave can be placed either: i) in the vicinity of thoracic or abdominal aorta (along the mid-sternal-umbilical line of the body)—for tracking of the central dynamical patterns (systemic blood pressure, cardiac output) versus local changes in the aorta, ii) above the location of major vessels in the portal system—for tracking dynamics of the portal pressure and portal hypertension, or iii) above the location of the major pulmonary vessels—for tracking dynamic changes in the pulmonary-artery/vein system and detecting pulmonary hypertension or pulmonary edema in patients with impaired cardiac function (heart failure, valve defects). The sensors for tracking the pressure wave signal can be also placed in the vicinity of carotid arteries on the neck (for example, a necklace) or over the head (for example, a headband), a wearable bag, pack, electrocardiographic electrode, belt, wristband, waist belt, vest, t-shirt and other clothes. The sensors for tracking the pressure wave described above (for example, an accelerometer, piezoelectric sensor or a photoplethysmographic sensor) can be either incorporated into a portable monitoring system (such as a Holter ECG monitor), ECG-electrodes, wearable belt, patch, close, armchair, car chair, bed/mattress. An example of one embodiment of such system is shown in FIG. 3. To improve the quality of the detection and monitoring of the pressure-wave signal, the sensors can be customized to combine convenience to the user/patient with the signal quality. For example, several piezoelectric, accelerometer or pressure-transducer sensors can be placed inside a wearable belt, and signals received from all these sensors could be processed and analyzed simultaneously, to improve the signal-to-noise ratio and extract the pressure-wave signal from noise. Among the methods that can be applied for such processing are: i) averaging the signals registered by several sensors (for example, sensors placed around the torso inside a wearable belt), ii) rejection of the noisy or uncharacteristic signals (that deviate from the standard pressure-waveform template), and iii) pattern-recognition and, in particular, the principal component analysis or other linear/nonlinear orthogonal/non-orthogonal transforms that extract typical features of the pressure waveform from the data recorded simultaneously by several sensors placed at different sites of the torso/body.

Alternatively, to minimize the number of sensors, the same sensor (s) can be used to record several blood (arterial) pressure waveforms at different locations around the body. In this case, the arterial-pressure waveforms are recorded non-simultaneously and later synchronized (time-aligned) to some fiducial point in the same phase of a cardiac cycle. An R-wave or some other part of the ECG signal can be used as a fiducial point for the time alignment of arterial-pressure signals recorded over different cardiac cycles.

Aligning, Normalizing and Averaging the Signals Registered by Several Sensors

If the sensors are placed at the same distance from the heart, they will register the pressure wave at the same time. The signals, therefore, can be represented as:

$$St=Sp+Sn, \qquad (3)$$

where St is the total signal registered by a sensor, Sp is the signal component due to the arterial pressure wave and Sn is the signal component due to ambient noises. Therefore, the contributions of Sp are similar for different sensors, whereas Sn, being more random, varies from sensor to sensor. Thus, a point-by-point averaging of the St registered by different sensors placed equidistantly from the heart will reduce the contribution of Sn component and increase the contribution of Sp (i.e., the signal-to-noise ratio, SNR).

If the sensors for registering the pressure wave signals are located at different distances from the heart (for example, along the thoracic and abdominal aorta), the pressure wave is registered by these sensors at different times. In that case, the signal can be represented as $$St=(Sp+\text{tau})+Sn, \qquad (4)$$

where St is the total signal registered by a sensor, Sp is the signal component due to the arterial pressure wave, tau is the time lag (shift, delay) between the times of arrival of the pressure wave at the locations of different sensors, and Sn is the signal component due to ambient noises. To reduce the contribution of Sn and increase the SNR, the analysis can be performed in 2 steps:

1) First, by varying the value of tau systematically (from 0 to the beginning of the next cardiac cycle), calculating the cross-correlation for each tau, and finding the value of tau that gives the maximum cross-correlation, one can determine the optimal value of tau for each sensor.
2) When the optimal values of tau (tau_opt) for each sensor are identified, a point-by-point averaging is performed for the time-aligned signals obtained by subtracting the tau-opt:

$$\text{Time\_aligned } St=(Sp-\text{tau\_opt})+Sn \qquad (5)$$

The shape of the Sp waveforms registered by different sensors can be slightly different:

$$St=(k*Sp+\text{tau\_opt})+Sn, \qquad (6)$$

where k represents a coefficient of expansion or contraction of the Sp signal. In this case, the pressure-wave signal can be obtained using the time-aligning step (3) followed by an analysis of cross-correlation coefficient (function) for different values of the coefficient k. Subsequently, the optimal value of k (k_opt) giving the maximum cross-correlation value can be used to obtain a time-aligned and normalized signal, which has a higher SNR with respect to Sp:

$$\text{Time-aligned\_\&\_normalized\_}St = (Sp/k\_\text{opt-tau\_opt}) + Sn \quad (7)$$

The Time-aligned_&_normalized_St can be obtained during the calibration step and later used as a template for the detection and dynamical tracking of changes in the arterial pressure waveforms. The calibration procedure can include identification of a personalized set of the Time-aligned_&_normalized_St for various body positions.

The processing algorithm described above can be further extended to include filtering, regression, pattern recognition methods (principal component analysis, independent component analysis, and nonlinear factorizations), time-series analysis and other statistical methods and methods of artificial intelligence.

Finding an Optimal Location of Sensors or Sensor Arrays

A further object of this invention is to identify the optimal location of the pressure sensor by registering and comparing the pressure waves from several locations, measuring the dynamic patterns of the pressure waves, adjusting the filtering cutoff values/model parameter/detection thresholds, as described above, and determining the location with the greatest signal-to-noise ratio for the optimal separation of local versus non-local dynamical patterns.

One approach for finding an optimal recording site is by estimating a correlation between the information (variance) of the signals obtained at different recording sites. A particular application of this approach for finding optimal electrocardiographic (ECG) recording sites has been described by R. L. Lux et al. (Lux R L, Smith C R, Wyatt R F, Abildskov J A. Limited lead selection for estimation of body surface potential maps in electrocardiography. IEEE Trans Biomed Eng. 1978; 25(3):270-6). As shown by Lux et al., the greatest average correlated power between a particular site and all other sites can be used as a criterion for selecting optimal sites. Other statistical estimators (the root-mean-square error, absolute error or entropy) can also be used for finding the optimal recording sites. In addition, pattern recognition can also be used for finding the optimal projection coefficients and basis functions with the greatest information (covariance) content. These include principal component analysis, independent component analysis, and other orthogonal, non-orthogonal, linear and non-linear projection methods. These and other applicable pattern-recognition methods have been disclosed by Shusterman in the application Ser. No. 12/885,520 filed Sep. 19, 2010, and U.S. Pat. Nos. 7,485,095, 7,343,197, 6,925,324, and 6,389,308. The disclosures contained in those Shusterman patents and application are, by reference, incorporated herein in their entireties.

Measurement of the Arterial Pressure Wave Characteristics in the Setting of Actively Induced Stimuli A further object of this invention is to measure pulse-wave velocity and pressure-wave characteristics in the setting of actively induced stimuli, sequences of stimuli/signals to improve the pressure-wave detection and discrimination. The stimuli may include mechanical, electrical and chemical signals. For example, a mechanical pulse can be given at the frequency of the pressure-pulse or its sub-harmonic to induce a stronger, resonant signal (or resonance) of the vascular walls at a particular frequency and phase, which would allow a more reliable detection of the pressure signal and its discrimination from noises.

A further object of this invention is to measure pulse-wave velocity and its characteristics in a setting of active stimulation by stimuli or sequences of stimuli/signals to induce a physiological response (reaction). This can be applied to: i) improve detection of the pressure signal and its discrimination from noises, ii) calibrate or test the measurement accuracy, or iii) analyze physiological responses to such stimulation for diagnosing a disorder/disease. For example, a mechanical/electrical energy (stimulus) can be applied to the neck to modify arterial pressure via a baroreflex. To determine at least one typical characteristic of the dynamical patterns associated with said stimulus versus those in the absence of such stimulus one can compare those patterns using a point-by-point comparison or subtraction of the data points obtained during the same phase of the cardiac cycle (time-aligned by the electrocardiographic R-wave, P-wave, T-wave, cardiac sound or some other marker of a cardiac-cycle phase), template matching, signal averaging and estimation of the root-mean-square error between the averaged template obtained in the stimulus-free setting and that obtained during the stimulus application, mathematical decomposition, pattern recognition, principal component analysis, independent component analysis, and other orthogonal, non-orthogonal, linear and non-linear projection methods. These and other applicable pattern-recognition methods have been disclosed by Shusterman in the application Ser. No. 12/885,520 filed Sep. 19, 2010, and U.S. Pat. Nos. 7,485,095, 7,343,197, 6,925,324, and 6,389,308. The disclosures contained in those Shusterman patents and application are, by reference, incorporated herein in their entireties.

This can facilitate initial calibration and subsequent testing of the system. In addition, this can also facilitate estimation of the individual's baroreflex and associated changes in the pressure waveform patterns, diagnosis of syncope, transient and nocturnal hypertension and hypotension.

A further object of this invention is to link the dynamics of at least one of: arterial pressure, cardiac output, pulmonary pressure/edema, vascular activity with a specific genetic variant, as described above and shown in FIG. 2.

A further object of this invention is to provide an ECG analyzing system that includes a monitoring device for receiving and analyzing ECG signals and which includes means for communicating with an external computer to which the ECG signals can be forwarded for more complex analysis. The monitoring device can be reprogrammed by the external computer to select the primary elements of the ECG signals that are unstable or abnormal. The low level analysis performed by the monitoring device is thus focused on the critical primary elements for that patient.

The system of the present invention can be used for management and analysis of electronic health (medical) records and information, analysis and management of biometric data, or information management of other types of healthcare data.

The system of the present invention provides instant access to information from a variety of distributed sources to reduce costs, improve quality of patient care and optimize decision making. For example, the system can be used to provide a real-time view of in-hospital patient distribution and operations structure in different departments and at different stages of the treatment process, from admission to discharge, or in the Emergency Room. The system can capture and integrate monitoring of vital signs, biometrical data, capture and integrate text, images, technical information related to device functioning and instrumentation status. The system can also provide an intelligent, tailored representation for different types of users and different points of care. For example, it can improve information sharing among the healthcare providers, including physicians, nurses, technicians, clerks, and others. The system of the present invention can also facilitate analysis, management, and optimization of information processing from the traditional departmental systems—e.g., legacy systems (Nursing, Pharmacy, LIS, RIS, PAS, by creating integrated database, applying intelligent analysis and optimizing diagnosis and treatment, including diagnostic and treatment plans and providing intelligent alarms and alerts to support and optimize clinical decision making.

The system of the present invention can collect real-time physiological and health data from a variety of sensors including vital sign monitors, ventilators, infusion pumps. It can also support a wide range of physiologic sensors from a variety of manufacturers. The system can also automatically re-configure itself to accept and recognize new data from physiological sensors whenever a new sensor is plugged into the system. It is also possible to enter new data into the system using an integrated barcode scanning or RFID tag or MEMS tag or other types of automatic entry of information at the bedside in a real time. The system of the present invention can also adapt, compare and merge new information with the data that already exist in the system. Because the information flow between different levels/units of the system is bi-directional, the system supports and optimizes seamless exchange of data coming from different diagnostic and treatment modalities, such as patient information from hospital data repositories (e.g., Laboratory, Medication, Admission/Discharge/Transfer and others) and intelligently alert the clinician to potential problems.

The system can also have multiple displays, terminals, including wireless connections with personal handheld devices (PDA, Smart Phones, Cell phones, computers, and computer tablets). Using these displays, users can simultaneously receive different modes of information, such as physiological signal information (vital signs, ECG, blood pressure, cardiac output), real-time intelligent alerts, prescription dispensing, drug interaction, dynamical report, individual patient dynamics, and serial comparison of individual patient's data, etc.

The genetic and/or molecular data can be obtained using a "Candidate Gene Approach", "Genome-wide Association" studies, gene sequencing, real-time or traditional polymerase chain reaction (PCR), micro-arrays, or other methods for the analysis of genetic data. Examples of genetic variants (polymorphisms) may include single nucleotide polymorphism (SNP), synonymous and nonsynonimous SNP, mutations, benign variants, common and rare variants, alleles, allele frequency and penetrance.

Example 1

Differentiating Genetic Etiologies of Brugada Syndrome

The results of the traditional heart rate variability (HRV) analysis in Brugada syndrome have been inconsistent. Since Brugada syndrome represents a polymorphic group of mutations, the inconsistencies could have resulted from the genotypic differences in the studied populations. The DPRL-Gene was tested in three genotypically distinct groups of individuals. DPRL-Gene provides a more detailed description of cardiac rhythm dynamics than the traditional HRV analysis by using multiple filtering cutoffs (scales). Therefore, DPRL-Gene captures scale-specific features that escape detection by the traditional HRV examination with a single cutoff value. Indeed, DPRL-Gene allowed detection of distinct patterns of cardiac rhythm in genotypically different populations with different prognosis.

In this example, DPRL-Gene quantifies patterns of cardiac rhythm in different genetic subtypes of Brugada syndrome by filtering the sequence of beat-to-beat intervals between successive cardiac beats (electrocardiographic RR intervals) through multiple filtering cutoffs, instead of a single cutoff value utilized in the traditional HRV. In subjects with abrupt, beat-to-beat irregularities and multiple pauses the higher cutoff value will cause a greater change in HRV (compared to a lower cutoff) than in subjects without such irregularities or pauses.

Thus, DPRL-Gene decomposes complex patterns of cardiac rhythm in order to identify its typical features. Compared to the filtering techniques that have been previously employed for cardiac-rhythm analysis (e.g. wavelet decomposition or principal component analysis), the advantages of DPRL-Gene are: 1) a clear association with the underlying physiological processes (beat-to-beat irregularities and pauses), 2) a direct use of well-established spectral HRV indices, whose physiological correlates have been documented in a number of experimental and clinical studies, and 3) a simple adjustment ("fine-tuning") of the filtering cutoffs to the specifics of a particular patient population.

DPRL-Gene extends the traditional HRV analysis, which utilizes constant filtering cutoffs, by using multiple cutoff values (scales) and tracking changes in the HRV indices associated with changes in these cutoffs. Specifically, two filtering cutoff, 75 milliseconds (ms) and 2000 ms, were used in this study to identify genotype-specific patterns of cardiac rhythm.

The DPRL-Gene algorithm consists of the following steps: 1) Series of RR-intervals are processed with the $1^{st}$ cutoff value (75 ms) by comparing each RR interval with a moving average of 5 consecutive RR-intervals centered at the RR-interval under examination (current RR). If the difference between current RR and the 5-beat moving average is greater than the 75-ms cutoff, than current RR is excluded from the analysis, and the resulting gap in the time series is linearly interpolated. The time and frequency domain HRV indices are computed from the resulting series of RR intervals as described above. 2) Step 1 is repeated and the HRV indices are computed again with the $2^{nd}$ cutoff value (2000 ms), and 3) Finally, the HRV indices obtained with the $1^{st}$ (Step 1) and $2^{nd}$ (Step 2) cutoffs are compared.

The rationale for using the 75-ms cutoff comes from my studies of HRV in various patient populations, which showed that such a cutoff allows inclusion of normal RR-intervals in most subjects with a normal sinus node function, while rejecting artifacts and outliers. Therefore, increasing the cutoff from 75 ms to 2000 ms does not cause major changes in the short-term HRV indices in most subjects. By contrast, in the individuals with a sinus node dysfunction, manifested by abrupt, beat-to-beat irregularities and pauses, the 2000-ms cutoff would lead to a substantial increase in HFP and RMSSD compared to the 75-ms cutoff value.

Patients.

Ambulatory electrocardiographic recordings from three groups of patients were used in this study. Group 1 (N=9) and Group 2 (N=6) were comprised from, respectively, genotypically affected and unaffected members of a large, multigenerational family with an A280V mutation in the GPD1-L gene on chromosome 3. This family includes 4 individuals with a history of syncope or near-syncope; three of those individuals had an Implantable Cardioverter-Defibrillator (ICD) placed. Several weeks after the implantation, one of those individuals had two appropriate ICD shocks for ventricular fibrillation; another individual had asymptomatic nonsustained ventricular tachycardia. Subjects in this family have a variable expression of classic ECG Brugada syndrome pattern, age-dependent penetrance, and male predominance. Direct sequencing was used to identify genotypically affected and unaffected family members. Group 3 (N=4) consisted of individuals with Brugada syndrome (not caused by GPD1-L) who were not members of Group's 1 family. In Group 3, three out of four individuals were from a single, moderate-sized family with a T353I mutation in the SCN5a sodium channel. In this family, both male and female carriers are highly symptomatic at young ages, have typical Brugada-type ECG changes and borderline prolongation of QT intervals.

Figure 1:
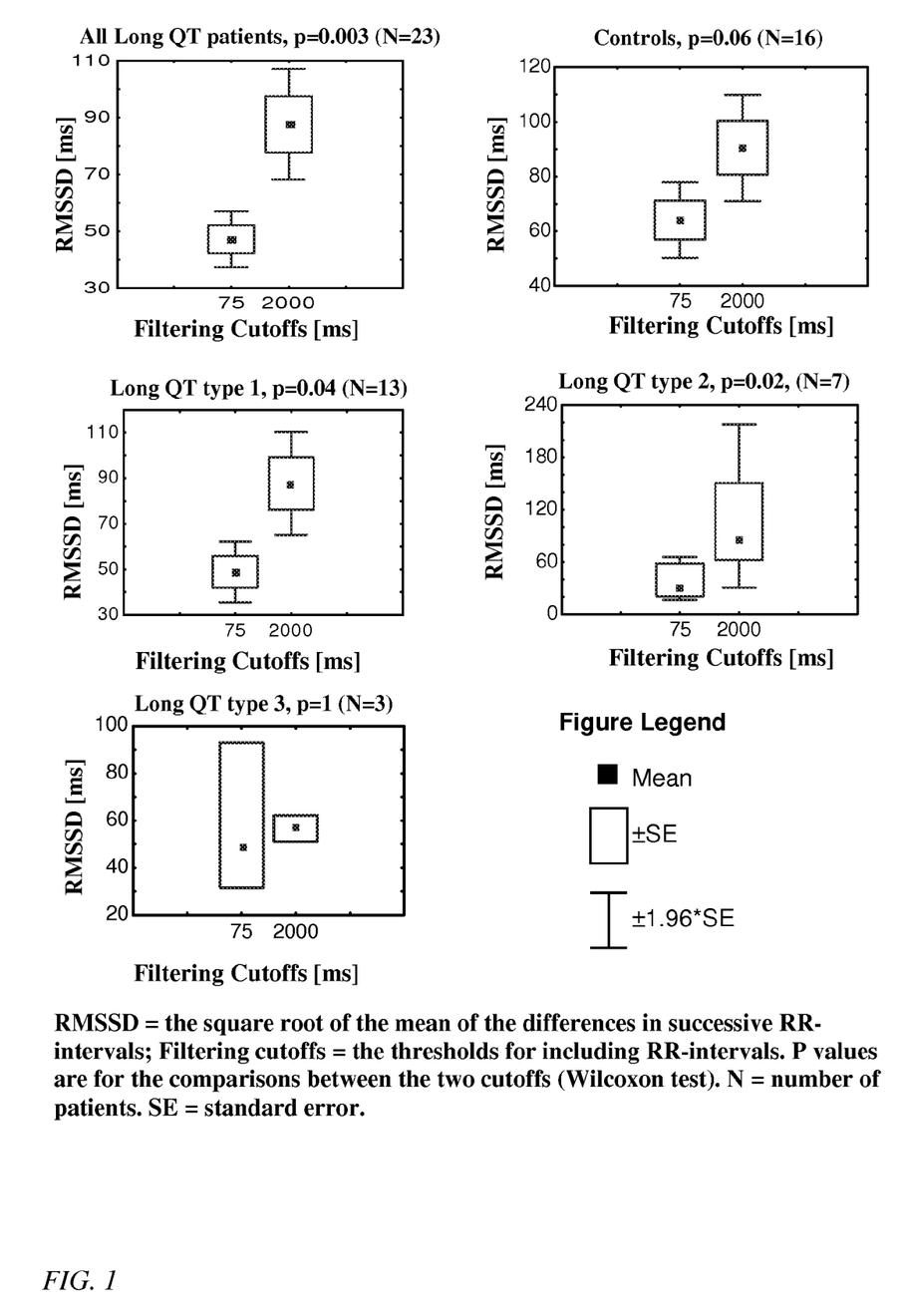
FIG. 1 is a graphical representation of the statistical results obtained using the method of present invention and revealing the differences between dynamic patterns of cardiac rhythm associated with different sub-types of Long QT syndrome.

LQTS-causing mutations might involve the sinus node, leading to aberrations in cardiac rhythm. To test this hypothesis, the features of cardiac rhythm in 23 genotyped patients with LQTS and 14 matched controls were examined using DPRL-Gene applied to Holter ECG data. DPRL-Gene was applied with two, experimentally selected moving-average cutoffs, 75 ms and 2000 ms for 5-beat averages to show the differences in dynamic patterns between the subtypes of LQTS (FIG. 1).

TABLE 1

Linkage between genetic etiologies of Brugada syndrome and dynamic patterns of cardiac rhythm using DPRL-Gene.

|  | Group 1 | Group 2 | Group 3 | $P_{1-2}$ | $P_{1-3}$ | $P_{2-3}$ |
|---|---|---|---|---|---|---|
| $SDNN_{75}$ index [ms] | 42.4 ± 10.7 | 62.5 ± 20.8 | 45.9 ± 15.7 | 0.03 | 0.64 | 0.22 |
| $RMSSD_{75}$ [ms] | 27.7 ± 11.6 | 44.5 ± 19.2 | 52.8 ± 26.8 | 0.05 | 0.03 | 0.58 |
| $RMSSD_{2000}$ [ms] | 32.4 ± 20.7 | 45.1 ± 20.1 | 104 ± 75.4 | 0.26 | 0.004 | 0.10 |
| *$RMSSD_{D-2000}$ [ms] | 11.3 ± 8.8 | 13.2 ± 8.0 | 28.1 ± 12.1 | 0.69 | 0.02 | 0.046 |
| *$RMSSD_{N-2000}$ [ms] | 24.1 ± 18.5 | 32.4 ± 12.4 | 81.8 ± 80.1 | 0.36 | 0.06 | 0.16 |

*subscripts D and N indicate data obtained during day and night time, respectively.
SDNN = standard deviation of the intervals between normal (sinus) cardiac beats, also referred to as the electrocardiographic RR-intervals;
RMSSD = the square root of the mean of successive differences of the intervals between normal (sinus) cardiac beats.

In genotypically unaffected individuals from Group 2, the change in filtering cutoff had a small effect on HRV (Table 1). In contrast, the same approach revealed much greater alterations in genotypically affected individuals from Groups 1 and 3. Furthermore, the structure of the changes in cardiac rhythm patterns was different in the two genotypically distinct groups. In Group 1, the short-term, "regular" HRV, estimated using the 75 ms cutoff, was lower compared to the other two groups, and there was no overlap between Groups 1 and 2 with respect to HFP. Yet, when the threshold was increased to 2000 ms, the differences between Groups 1 and 2 became smaller or disappeared due to the predominant increase in the short-term sinus node irregularity in Group 1. At the same time, the differences between Groups 1 and 3 became larger with the 2000 ms cutoff, indicating that Group 3 had an even greater proportion of abrupt beat-to-beat irregularities and pauses than Group 1. Furthermore, with the 2000 ms cutoff, $RMSSD_{D-2000}$, a measure of short-term beat-to-beat irregularity in Group 3 became significantly higher than that in unaffected subjects from Group 2 (p=0.046).

Thus, DPRL-Gene revealed enhanced beat-to-beat irregularities in the two genotypically distinct groups of individuals with Brugada syndrome (Groups 1 and 3) compared to unaffected individuals (Group 2). In addition, it showed that abrupt irregularities were more prevalent in Group 3 compared to Group 1. This enhanced sinus node dysfunction observed in Group 3 of our study was associated with relatively high propensity for arrhythmic and syncopal events, and prolongation of QT-intervals. By contrast, subjects from Group 1 had a low incidence of events and a better prognosis.

Example 2

Differentiating Genetic Subtypes of Long QT Syndrome

The Long QT Syndrome (LQTS) is caused by mutations involving key cardiac ion channels. Different mutations are associated with specific modes of arrhythmia initiation and distinct changes in cardiac rhythm prior to these events. Some Other Potential Applications of this Invention Include:
   Analysis of patterns of T-wave alternans, repolarization and/or depolarization instabilities, QT-interval, and ECG patterns associated with different genetic variants and risk of disorders/death and screening/risk assessment for disorders/death;
   Analysis of various sleep patterns and sleep disordered breathing patterns associated with various genetic variants and screening/risk assessment for disorders/death;
   Analysis of ECG (T-wave alternans, instabilities, QT-interval, and waveform/morphology changes), breathing, and other health data before/during/after physical activity, sports, or psychological/mental stress associated with various genetic variants and screening/risk assessment for disorders/death;
   Analysis of ECG (T-wave alternans, instabilities, QT-interval, and waveform/morphology changes), breathing, and other health data before/during/after daily activities associated with various genetic variants and screening/risk assessment for disorders/death.

The above and other objects and advantages of this invention will be more fully understood and appreciated by reference to the following description and the drawings.

Figure 2:
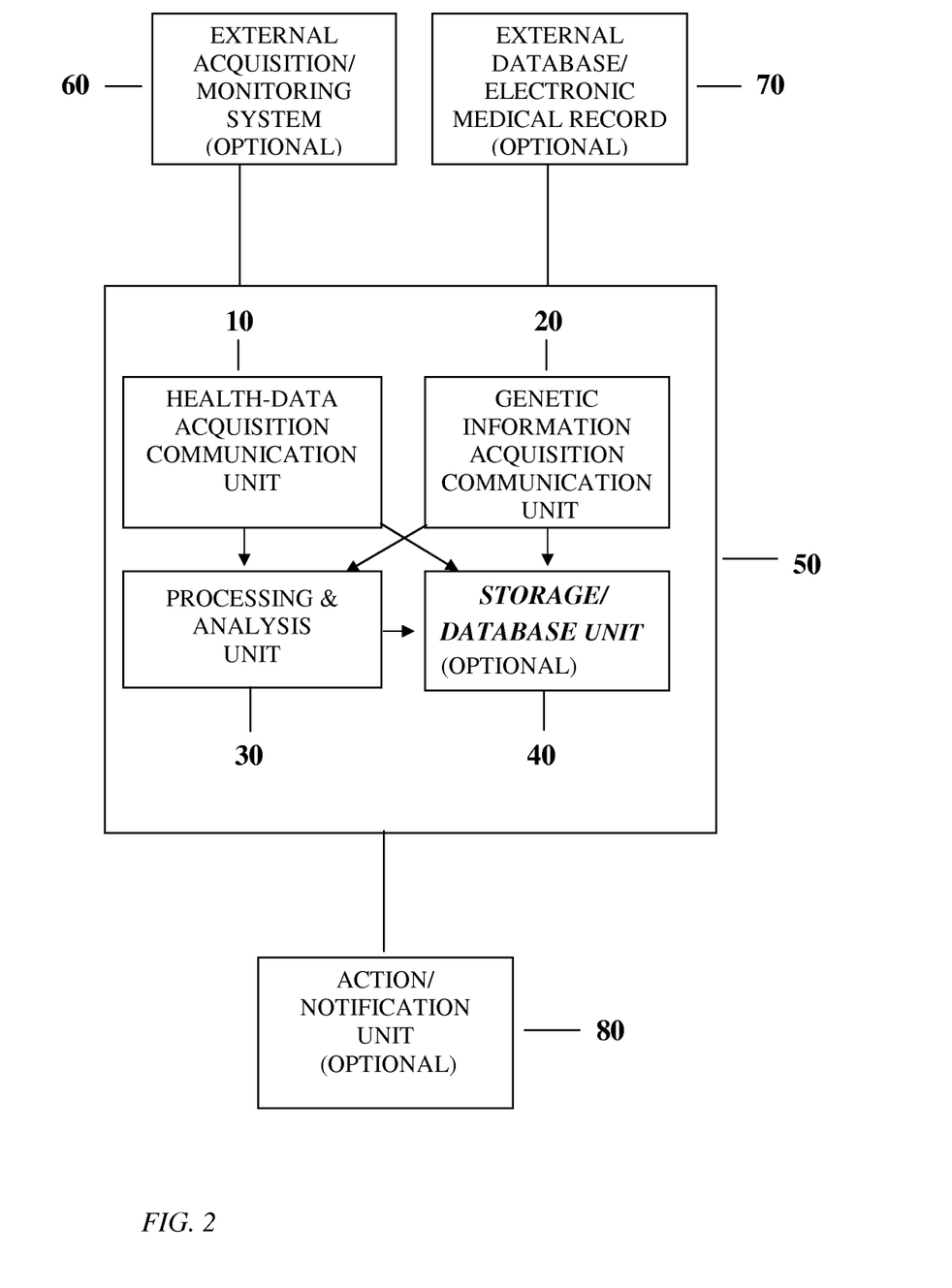
FIG. 2 is a block diagram of the method and system of the preferred embodiment of this invention.

FIG. 2 is a block-diagram of a preferred embodiment of a system for analyzing the linkage between dynamic patterns of health data and genetic variants. The system 50 may receive physiological or health data (for example, ECG data) from a recorded data source for analysis or receives the data in a real time, on-line; these data can be received from an external acquisition/monitoring system 60 or an external database/electronic medical record system 70. The communication between the system 50 and the external systems 60 and 70 can be bi-directional, so that the results of analysis from system 50 can be sent to the external database 70 or can be used for "fine-tuning" the monitoring system 60. The system of the present invention includes "Health-data acquisition/communication" unit 10, "Genetic-information acquisition/communication" unit 20, "Processing and analysis" unit 30 and an optional "Storage/database" unit 40. The processing unit 40 (or, alternatively, the implementation of the entire system 50) can be: i) a typical computer or personal computer of the type available from many vendors such as IBM and Hewlett-Packard, ii) a mobile computing device, such as a cell phone/Smart Phone/Personal Digital Assistant (PDA), or iii) a specialized processor (for example, MSP-430, Texas Instruments). The processing unit 40 receives the information from units 10 and 20 to identify characteristic features of the dynamic patterns of health-data associated with a specific genetic variant. These specific features can be identified by the methods described in examples presented above or by the signal-processing, pattern-recognition, statistical, mathematical modeling and time-series analysis methods described in the U.S. Pat. Nos. 6,389,308, 6,925,324, and 7,343,197 to Shusterman. When such features linking genetic variants to dynamic patterns in health data are identified, the filtering cutoffs or the pattern-recognition coefficients (for example, the coefficients in the Fourier transform, the Karhunen-Loeve transform, Laplace transform or other linear orthogonal/nonorthogonal transforms) are adjusted to allow i) optimal identification of the dynamic patterns associated with: a particular genetic variant or ii) optimal separation of the patterns associated with different genetic variants, as illustrated in the examples provided above. The health-data, genetic information and the results of analysis from units 10, 20, and 30 could be stored in the optional internal storage/database unit 40 (for example, a solid-state memory card, such a Secure Digital (SD) card or a micro-SD card). The storage unit 40 can be also an internal memory module of a cell phone or an external memory module.

FIG. 3 is a block diagram of another important embodiment of the method and system of this invention for tracking the dynamical patterns of at least one of: systemic blood pressure, cardiac output, peripheral resistance/vascular compliance, pulmonary-artery pressure, portal-system pressure, pulmonary edema, and aneurisms of aorta.

The system 50 receives information collected over at least several seconds and, preferably, longer time intervals, from a sensor for detection of the start of pressure wave 60 and a sensor for detection of the local pressure wave 70. The sensor 60 can detect either an electrical activity of the heart (i.e. cardiac electrical depolarization or R-wave of the electrocardiogram) using standard ECG electrodes and circuitry or detect mechanical/acoustic activity of the heart as described in the Summary of this invention above. The sensor or sensors 70 are placed in the vicinity of one of the central, major vessels of the torso to detect and track the dynamic patters of local pressure waves when they arrive to the part of the vessel located close to the sensor. The sensor 70 can detect mechanical/acoustic activity of the heart as described in the Summary of this invention above. The sensors 70 may also include sensors located on the peripheral vessels (on the extremities, radial artery, hands, fingers, legs, feet or toes) to measure the dynamical patters of pressure waves in those peripheral vessels. Unit 10 receives the information from both sensors 60 and 70, to estimate pulse-transit time and local pressure parameters. Unit 10 also sends these estimates to Unit 30, which uses a mathematical (statistical) model to calculate dynamic patterns of blood pressure, cardiac output, vascular tone, and local-vessel's health/impairment (aneurisms). The system 50 may also include an optional Genetic Information Acquisition and Communication unit that, if included, can provide genetic information to Unit 30, which can use this information to identify the links between the dynamic patterns of health data (blood pressure, cardiac output, vascular tone, and local-vessel's health/impairment, including aneurisms) and specific genetic variants, as described above. The system 50 may also include an optional Storage/Database unit 40, which can store the data collected by the system as well as the results of system's 50 analysis. The system 50 may also include an optional unit 80, which can generate an alarm/notification if significant changes are detected. For example, the unit 80 may be represented by a wireless communication module/device, such as Bluetooth, Zigbee, cell phone, smart phone, personal digital assistant (PDA), Wi-Fi, wireless network, wireless connection to the Internet, fast-speed router, intranet or other types of radio-frequency communication and non-wireless communication. The notification can be sent to the central server or from the central server to a cell phone of a medical professional, to notify paramedics or attending physicians about emergency condition that requires immediate intervention, or to send instructions/notifications to a patient to stop all activities, take a medication, change the speed/intensity of physical activity, contact medical center and so on. The unit 80 may be also used to take an action by modifying the monitoring program (for example, adapting, individually tailoring the cutoff values or modeling parameters), initiating cardiac pacing or defibrillation, modifying the angle of a recliner bed (in patients with unstable blood pressure), modifying the speed of a treadmill, and other monitoring, testing or patient management parameters.

Whereas particular aspects of the method of the present invention and particular embodiments of the invention have been described for purposes of illustration, it will be appreciated by those skilled in the art that numerous variations of the details may be made without departing from the invention or the scope of the appended claims.

What is claimed is:

1. A method useful in monitoring of at least one feature of a wave signal selected from blood pressure, cardiac output and vascular activity comprising:

placing at least one sensor adapted for registering at least one mechanical movement on the surface of a torso in the vicinity of at least one major blood vessel;

collecting information from said at least one sensor over multiple cardiac cycles;

processing said information by at least one signal processing method selected from time aligning the information registered from multiple cardiac cycles with respect to a fiducial point corresponding to the same phase of each cardiac cycle, signal averaging, filtering, pattern recognition, and time-series analysis to improve the signal-to-noise ratio of collected information respecting said at least one feature of a wave signal being monitored; and adjusting at least one point-by-point comparison of the signals recorded during the same phase of a cardiac cycle at different anatomical locations, time alignment of the signals by finding the time lag corresponding to the maximum value of the cross-correlation function, normalization of the signals by finding the stretching/compression coefficients that maximize the cross-correlation function and normalizing the waveform duration/amplitude by these coefficients, rejection of the noisy or uncharacteristic signals that deviate from the standard pressure-waveform template, averaging of the signals registered by several sensors with a time alignment and normalization as necessary, a mathematical decomposition, pattern recognition, principal component analysis and other orthogonal and non-orthogonal transforms that extract typical features of the pressure waveforms.

2. A method as set forth in claim 1 in which said at least one major blood vessel is selected from the aorta, ascending aorta, thoracic aorta, abdominal aorta, pulmonary artery, pulmonary vein, hepatic portal vein and kidney arteries.

3. A method as set forth in claim 1 in which a sensor is placed in the vicinity of a non-central artery to obtain a signal related to blood pressure wave in the non-central artery and compare said signal with that registered in the vicinity of a central artery and to separate peripheral vascular activity from the systemic blood pressure.

4. A method as set forth in claim 1 in which said at least one sensor is selected from at least one accelerometer, micro-electro-mechanical (MEMS) sensor, infrared, and pulse oximetry sensor.

5. A method as set forth in claim 1 which includes adjusting at least one analysis, processing, filtering and pattern-recognition method, cutoff value, threshold, and model parameter in the setting of at least one actively induced mechanical, electrical and chemical stimulus and sequences of stimuli to improve the pressure-wave detection and discrimination.

6. A method as set forth in claim 5 in which said stimulus is given at the frequency of at least one pressure-pulse and its sub-harmonic to induce a stronger, resonant signal of the vascular walls at a particular frequency and phase to allow a more reliable detection of the pressure signal and its discrimination from noises.

7. A method as set forth in claim 5 in which said stimulus is applied to improve at least one detection of blood pressure signal and its discrimination from noises, system calibration, analysis of physiological responses to said stimulus and diagnosis of syncope, transient hypertension and hypotension.

8. A method as set forth in claim 5 in which said stimulus is applied to modify arterial pressure for at least one system calibration and estimation of an individual's baroreflex and associated changes in the pressure waveform.

9. A method as set forth in claim 1 in which said at least one sensor is placed in the vicinity of a large artery on at least one part of a body selected from the chest and abdomen.

10. A method as set forth in claim 1 in which multiple sensors are applied for analyzing at least one feature selected from registering and comparing the pressure waves from several locations, measuring the dynamic patterns of the pressure waves, adjusting the filtering cutoff values, model parameter, detection thresholds, determining the location with the greatest signal-to-noise ratio, and the optimal separation of local versus non-local dynamical patterns.

11. A system for monitoring at least one feature of a wave signal selected from blood pressure, cardiac output and vascular activity comprising:
at least one sensor adapted for registering at least one mechanical movement on the surface of a torso in the vicinity of a major blood vessel;
at least one acquisition and communication unit for receiving and recording information from said at least one sensor over multiple cardiac cycles; and
at least one processing unit adapted to process said information by at least one signal processing method selected from time aligning the information registered from multiple cardiac cycles with respect to a fiducial point corresponding to the same phase of each cardiac cycle, signal averaging, filtering, pattern recognition, and time-series analysis to improve the signal-to-noise ratio of collected information respecting said at least one feature of a wave signal being monitored, and further adapted to process said information from several anatomical locations using at least one processing method selected from point-by-point comparison of the signals recorded during the same phase of a cardiac cycle, time-alignment of the signals by finding the time lag corresponding to the maximum value of the cross-correlation function, normalization of the signals by finding the stretching/compression coefficients that maximize the cross-correlation function and normalizing the waveform duration/amplitude by these coefficients, rejection of the noisy or uncharacteristic signals that deviate from the standard pressure-waveform template, averaging of the signals registered by several sensors at different anatomical locations with a time-alignment and normalization as necessary, a mathematical decomposition, pattern recognition, principal component analysis and other orthogonal and non-orthogonal transforms that extract typical features of the pressure waveforms.

12. A system as set forth in claim 11 which includes at least one sensor adapted to be contained inside at least one carrier selected from a wearable bag, pack, electrocardiographic electrode, belt, necklace, headband, wristband, waist belt, vest, t-shirt, other clothes, patch, armchair, car chair, bed and mattress.

13. A system as set forth in claim 11 in which said at least one sensor is selected from an accelerometer, micro-electro-mechanical (MEMS) sensors, photoplethysmographic, infrared and pulse oximetry sensor.

14. A system as set forth in claim 11 in which said at least one sensor is placed in the vicinity of a blood vessel to measure local changes in the pressure waves' patterns associated with at least one type of an aneurism, atherosclerosis, portal hypertension, pulmonary hypertension and vascular disease.

15. A method for monitoring at least one vital sign selected from blood pressure, cardiac output and vascular activity comprising:
positioning at least one accelerometer sensor on an individual in the vicinity of at least one major blood vessel;
collecting and recording data relating to the individual's blood pressure wave at different anatomical locations from said at least one accelerometer sensor; and
processing said data by at least one signal processing method selected from time aligning the information registered from multiple cardiac cycles with respect to a fiducial point corresponding to the same phase of each cardiac cycle, signal averaging, filtering, pattern recognition, and time-series analysis, and further processing said data with respect to said anatomical locations using at least one processing method selected from point-by-point comparison of the signals recorded during the same phase of a cardiac cycle, time-alignment of the signals by finding the time lag corresponding to the maximum value of the cross-correlation function, normalization of the signals by finding the stretching/compression coefficients that maximize the cross-correlation function and normalizing the waveform duration/amplitude by these coefficients, rejection of the noisy or uncharacteristic signals that deviate from the standard pressure-waveform template, averaging of the signals registered by several sensors at different anatomical locations with a time-alignment and normalization as necessary, a mathematical decomposition, pattern recognition, principal component analysis and other orthogonal and non-orthogonal transforms that extract typical features of the pressure waveforms.

16. A method as set forth in claim 15 in which said at least one major blood vessel is selected from the aorta, ascending aorta, thoracic aorta, abdominal aorta, pulmonary artery, carotid arteries, kidney arteries, femoral arteries, hepatic portal vein and pulmonary vein.

17. A method as set forth in claim 15 in which a sensor is placed in the vicinity of a non-central artery to obtain a signal related to blood pressure wave in the non-central artery and compare said signal with that registered in the vicinity of a central artery and to separate peripheral vascular activity from the systemic blood pressure.

18. A system for monitoring at least one vital sign selected from blood pressure, cardiac output and vascular activity comprising:
- at least one accelerometer sensor adapted for registering at least one mechanical movement on the surface of a torso in the vicinity of a major blood vessel;
- at least one acquisition and communication unit for receiving and recording information from said at least one sensor over multiple cardiac cycles; and
- at least one processing unit adapted to process said information by at least one signal processing method selected from time aligning the information registered from multiple cardiac cycles with respect to a fiducial point corresponding to the same phase of each cardiac cycle, signal averaging, filtering, pattern recognition, and time-series analysis, and further adapted to process said information from several anatomical locations using at least one processing method selected from point-by-point comparison of the signals recorded during the same phase of a cardiac cycle at different anatomical locations, time alignment of the signals by finding the time lag corresponding to the maximum value of the cross-correlation function, normalization of the signals by finding the stretching/compression coefficients that maximize the cross-correlation function and normalizing the waveform duration/amplitude by these coefficients, rejection of the noisy or uncharacteristic signals that deviate from the standard pressure-waveform template, averaging of the signals registered by several sensors with a time alignment and normalization as necessary, a mathematical decomposition, pattern recognition, principal component analysis and other orthogonal and non-orthogonal transforms that extract typical features of the pressure waveforms, to improve the signal-to-noise ratio of collected information respecting said at least one vital sign being monitored.

19. A system as set forth in claim 18 in which said at least one sensor is placed in the vicinity of a blood vessel to measure local changes in the pressure waves' patterns associated with at least one type of an aneurism, atherosclerosis, portal hypertension, pulmonary hypertension and vascular disease.

* * * * *

UNITED STATES PATENT AND TRADEMARK OFFICE
CERTIFICATE OF CORRECTION

Page 1 of 1

PATENT NO. : 8,706,464 B2
APPLICATION NO. : 13/017043
DATED : April 22, 2014
INVENTOR(S) : Vladimir Shusterman It is certified that error appears in the above-identified patent and that said Letters Patent is hereby corrected as shown below:

On the Title page, item [54] and in the specification, column 1, title should read as follows:

"Method and System Useful in Analyzing and Monitoring Blood Pressure, Cardiac Output and/or Vascular Activity"

Signed and Sealed this
Twenty-second Day of July, 2014

Michelle K. Lee
*Deputy Director of the United States Patent and Trademark Office*